US005850018A

United States Patent [19]

Baszczynski et al.

[11] Patent Number: 5,850,018
[45] Date of Patent: Dec. 15, 1998

[54] EXPRESSION CONTROL SEQUENCE FOR GENERAL AND EFFECTIVE EXPRESSION OF GENES IN PLANTS

[75] Inventors: Chris Baszczynski, Urbandale; Eric Barbour, Des Moines, both of Iowa; Jeannine Horowitz, Coral Gables, Fla.; Jeffrey L. Rosichan, Burnsville, Minn.

[73] Assignee: Pioneer Hi-Bred International, Inc., Des Moines, Iowa

[21] Appl. No.: 686,417

[22] Filed: Jul. 26, 1996

Related U.S. Application Data

[60] Provisional application No. 60/001,552 Jul. 27, 1995.
[51] Int. Cl.$^6$ .............................. A01H 1/04; C12N 15/82; C07H 21/02
[52] U.S. Cl. ...................... 800/235; 800/205; 435/69.1; 435/172.3; 435/320.1; 435/410; 435/412; 435/420; 435/424; 536/23.1; 536/24.1; 514/44
[58] Field of Search ............................... 455/69.1, 6, 410, 455/420, 412, 424, 320.1, 172.3; 536/24.1, 23.1; 514/44; 800/205, 235, 255

[56] References Cited

U.S. PATENT DOCUMENTS 5,187,267  2/1993  Comai et al. .......................... 536/23.1

FOREIGN PATENT DOCUMENTS

WO 93/07278  A  4/1993  WIPO .

OTHER PUBLICATIONS

Stull et al. Phesm. Res. 12:465–483 (1995).
Koziel et al. Plant Molecules Biology 32:393–405 (1996).
Bessoule, J.–J., *FEBS Letters*, vol. 323, No. 1,2, pp. 51–54 (1993).
Das, P. et al., *Database Embl*, Heidelberg, BRD AC X56118, 10 Feb. 1992: "Nucleotide Sequence Footprints of Gene Conversion at the 27kD Zein Locus in Maise" (XP002030975), Genomics, vol. 11, pp. 849–856 (1991).
Shen, B. et al., *Database Embl*, Heidelberg, BRD AC T23314, 21 Jul. 1994: "Partial Sequencing and Mapping of Clones From Maize cDNA Libraries" (XP002030961), PMB vol. 26, No. 4, pp. 1085–1101.
Zhu, J.–K. et al., *The Plant Cell*, vol. 5, pp. 341–349 (1993).
Albani, D. et al., "A *Brassica napus* gene family which shows sequence similarity to ascorbate oxidase is expressed in developing pollen. Molecular characterization and analysis of promoter activity in transgenic tobacco plants," *The Plant Journal* (1992) 2:331–342.
An, G. et al., "Organ–Specific and Developmental Regulation of the Nopaline Synthase Promoter in Transgenic Tobacco Plants," *Plant Physiology* (1988) 88:547–552.
Anzola, J. et al., "Characterization of a *Borrelia burgdorferi dnaJ* Homolog," *Infection and Immunity* (1992) 60:4965–4968.

Atencio, D.P. et al., "MAS5, a Yeast Homolog of DnaJ Involved in Mitochondrial Protein Import," *Molecular Cellular biology* (1992) 12:283–291.
Bardwell, J.C.A. et al., "The Nucleotide Sequence of the *Escherichia coli* K12 dnaJ$^+$Gene,"*The Journal of Biological Chemistry* (1986) 261:1782–1785.
Bessoule, J.–J. "Occurrence and sequence of a DnaJ protein in plant (*Allium porrum*) epidermal cells," *FEBS Lett* (1993) 323:51–54.
Bessoule, J.–J. et al., "Cloning of a new isoform of a DnaJ protein from *Allium porrum* epidermal cells," *Plant Physiol Biochem* (1994) 32:723–727.
Caplan, A.J. et al., "Characterization of YDJ1: A Yeast Homologue of the Bacterial dnaJ Protein," *Journal of Cell Biology* (1991) 114:609–621.
Christensen, A.H. et al., "Maize polyubiquitin genes: structure, thermal perturbation of expression and transcript splicing, and promoter activity following transfer to protoplasts by electroporation," *Plant Molecular Biology* (1992) 18:675–689.
Depicker, A. et al., "Nopaline Synthase: Transcript Mapping and DNA Sequence," *Journal of Molecular and Applied Genetics* (1982) 1:561–573.
Guerrero, F.D. et al., "Promoter sequences from a maize pollen–specific gene direct tissue–specific transcription in tobacco," *Mol Gen Genet* (1990) 224:161–168.
Hudspeth, R.L. et al., "Structure and expression of the maize gene encoding the phosphoenolpyruvate carboxylase isozyme involved in $C_4$ photosynthesis," *Plant Molecular Biology* (1989) 12:579–589.
Narberhaus, F. et al., "Molecular Characterization of the *dnaK* Gene Region of *Clostridium acetobutylicum*, Including *grpE*, *dnaJ*, and a New Heat Shock Gene," *Journal of Bacteriology* (1992) 174:3290–3299.
Odell, J.T. et al., "Identification of DNA sequences required for activity of the cauliflower mosaic virus 35S promoter, "*Nature*(1985) 313:810–812.
Preisig–Müller, R. et al., "Plant dnaJ Homologue: Molecular Cloning, Bacterial Expression, and Expression Analysis in Tissues of Cucumber Seedlings," *Archives of Biochemistry and Biophysics* (1993) 305:30–37.
Twell, D. et al., "Promoter analysis of genes that are coordinately expressed during pollen development reveals pollen–specific enhancer sequences and shared regulatory elements," *Genes & Development* (1991) 5:496–507.
van Asseldonk, M. et al., "Cloning, Nucleotide Sequence, and Regulatory Analysis of the *Lactococcus lactis dnaJ* Gene," *Journal of Bacteriology* (1993) 175:1637–1644.
Zhu, J.–K. et al., "Expression of an *Atriplex nummularia* Gene Encoding a Protein Homologous to the Bacterial Molecular Chaperone DnaJ," *The Plant Cell* (1993) 5:341–349.

*Primary Examiner*—John L. LeGuyader
*Attorney, Agent, or Firm*—Pioneer Hi–Bred International, Inc.

[57] ABSTRACT

An expression control sequence which is intermediate in tissue specificity between constitutive and tissue specific is disclosed. This promoter is effective in expressing genes in the majority of tissues of corn, and can be used for effective expression of desired protein genes in plants.

16 Claims, 5 Drawing Sheets

```
      GGGTTTGAGCTCAAGCCGCAACAACAAATTTCGGTGCTCCCAAGCTTCATAAAGGCTATC
-758  TTCGGCGTCGTTGGGATCCATGGTGGCACAGAATCGAGTTGATGTTGTAGCTGGCGGCTA
-698  GGGTTTGAAGTGGAGAAGAGGTCCGGCTGGTGGCATCCTATCGTCTATTGAGGGTTGGGT
-638  CCGGTGGCATCATACTTGATGACAATTGAAAGTAATTTTAATCAACTTGTCATGAGTAGT
-578  GAGTCTTTTATAAAAAATAAGCTGAAATAAGCACCCTTTGATGAGCTTATAGGATTATCA
-518  TAATCTCAAATGCTAAATTATATAATTTTATTAGATAAGTTGCTTGTTTGTTTCCCCACT
-458  AGCTTATTTACATTGGATTATATAATCTACATAAATTATAATCTCAAACAAAAAGTCCTT
-398  AATCAGAGATCAGCGAGGTCTCACGAGTGAGAAGGCGAGAGCTTGTCCAAACGAGCATTT
-338  TCGGCCGTGTGAACACCCATTTCAGCAAAGCCGTCGTTGTCCAGTTCAGCGAAGCGCATT
-278  CTGCGGCTTTGGCGTGACCCATTCTGCTAGCTCAGCACTGAGAATACGCGTCCGCTGCAG
-218  CGTTGGCGTACAGGCCGGACTACATTAGCCAACGCGTATCGGCAGTGGCAAACCTCTTCG
-158  CTTCTAACTCCGCTGGGCCACCAGCTTTGACCGCCGCCTCCCTTCCCCTCCGCTACTGCT
 -98  CCTCCCCACCCCACTCCCCCGCAGGAGCGGCGGCGGCGGCGAGGTCGTACCCCACAT
 -38  CGGCGAGCGGCGGCGGCACCGCCGGAGGCAAAGGCAAGTCTAGATCTAACCC
```

FIG. 1

```
 -812 GAGCTCAAGCCGCAACAACAAATTTCGGTGCTCCCAAGCTTCATAAAGGCTATCTTCGGC
 -752 GTCGTTGGGATCCATGGTGGCACAGAATCGAGTTGATGTTGTAGCTGGCGGCTAGGGTTT
 -692 GAAGTGGAGAAGAGGTCCGGCTGGTGGCATCCTATCGTCTATTGAGGGTTGGGTCCGGTG
 -632 GCATCATACTTGATGACAATTGAAAGTAATTTTAATCAACTTGTCATGAGTAGTGAGTCT
 -572 TTTATAAAAAATAAGCTGAAATAAGCACCCTTTGATGAGCTTATAGGATTATCATAATCT
 -512 CAAATGCTAAATTATATAATTTTATTAGATAAGTTGCTTGTTTGTTTCCCCACTAGCTTA
 -452 TTTACATTGGATTATATAATCTACATAAATTATAATCTCAAACAAAAAGTCCTTAATCAG
 -392 AGATCAGCGAGGTCTCACGAGTGAGAAGGCGAGAGCTTGTCCAAACGAGCATTTTCGGGC
 -332 GTGTGAACACCCATTTCAGCAAAGCCGTCGTTGTCCAGTTCAGCGAAGCGCATTCTGCGG
 -272 CTTTGGCGTGACCCATTCTCCTAGCTCAGCACTGAGAATACGCGTCCGCTGCAGCGTTGG
 -212 CGTACAGGCCGGACTACATTAGCCAACGCGTATCGGCAGTGGCAAACCTCTTCGCTTCTA
 -152 ACTCCGCTGGGCCACCAGCTTTGACCGCCGCCTCCCTTCCCCTCCGCTACTGCTCCTCCC
  -92 CACCCCACTCCCCCGCAGGAGCGGCGGCGGCGGCGGCGAGGTCGTACCCCACATCGGCGA
  -32 GCGGCGGCGGCACCGCCGGAGGCAAAGGCAAGATGTTCGGGCGCGCGCCGAAGAAGAGCG
                                     M  F  G  R  A  P  K  K  S  D
   29 ACAACACCAAGTACTACGAGATCCTCGGGGTGCCCAAGTCGGCGTCCCAGGACGATCTCA
         N  T  K  Y  Y  E  I  L  G  V  P  K  S  A  S  Q  D  D  L  K
   89 AGAAGGCCTACCGCAAGGCTGCTATCAAGAACCACCCCGACAAGGGCGGTGACCCCGAGA
         K  A  Y  R  K  A  A  I  K  N  H  P  D  K  G  G  D  P  E  K
  149 AGgtccggaccaccccctctcccctcttgcgatctggccttgatccgatctggcgtgatc
  209 cgttgcggtagatcgaggttctcggcagcctcgcgtctggtagatttacctcaggaagg
  269 gttgcatgttggtcttgatgtttaggtttggattcctcgtcctcggtagattcgttgatg
  329 cttctgtaggtaacaagccgcgattggtagttcctgttgcatgcgctggtttgtggtggt
  389 cgattcgcggtcatgtgtaccatgattgcgaccttagttgcgtaggggattcgcgagaac
  449 catctccgtgtgcttgctgcggtcagaatcctaagcaggtgaaaccgaacagttttttag
  509 cttgcatgccatgtgcggttctcgcggtcatgtgttatgaacttgtgattcacctcgcac
  569 atgtatattggctagtatttcttttcgatgacaggcaacgacgcaacgtcgcagctggc
  629 tcaggtgcaaacatttgtagttgggggttttcatcgatttttagtagtgcctgcattgt
  689 tcatttgtgctgcaggttgctcagttacatggtaaccaagatgcatggtggttataatt
  749 catttctccagatatttattactctaatggttgtgttatataatcatggcctcatgggaa
  809 gcctatccttgtcaccttgtttcagcaaggcatctgtggtcatccaggagctgttcaata
  869 tctgtttgctttaccttgattgccctttttgtatgttcctaggctttttctgtccgttatg
  929 tagcatattgtgtgttttcttatcttgtgaagcttagaaggtttgcttgtttggtataat
  989 cacctggagatcattggctgtattccttttgtattaaaactcgtgttttttttttttgcag
 1049 atgttacatgtgtttccaccacattatttgagccagtaatattgttttgcaggctatat
 1109 gattgttctatttcttgcttattttgtataccataatagtgctgctatatacaatgatga
 1169 ttttgtttaataaaaaaacatatatagaagtgacggatgtaaagatatatgttctcttca
 1229 actagttcagtctgtcagctaaatttcttttttgattcatgattttgtagagtaaaatctt
 1289 tattttaatttatttcagTTCAAGGAGCTCGCACAAGCCTATGAGGTTTTGAGTGATCC
                     F  K  E  L  A  Q  A  Y  E  V  L  S  D  P
 1349 AGAGAAACGTGAGATTTATGATCAGTATGGTGAAGATGCCCTTAAGGAAGGAATGGGCGG
         E  K  R  E  I  Y  D  Q  Y  G  E  D  A  L  K  E  G  M  G  G
 1409 TGGAGGATCCCATGTTGATCCATTTGACATCTTCTCATCATTTTTTGGACCCTCTTTTGG
         G  G  S  H  V  D  P  F  D  I  F  S  S  F  F  G  P  S  F  G
 1469 AGgtattgtacccatattcatttgtgactgttttttttggtacgctcctttatcaaatgtg
         G
```

FIG. 2A

```
1529  ataatgactggcttttatttgttttatttgcagGAGGTGGTGGAAGCAGCAGGGGAAGAA
                                       G  G  G  S  S  R  G  R  R
1589  GGCAAAGGAGGGGAGAAGATGTAGTTCACCCACTTAAAGTTTCTCTGGAAGATCTTTACA
      Q  R  R  G  E  D  V  V  H  P  L  K  V  S  L  E  D  L  Y  N
1649  ATGGCACCTCAAAGAAGCTCTCTCTTTCGCGCAATGTCATCTGCTCCAAGTGCAAGGGgt
      G  T  S  K  K  L  S  L  S  R  N  V  I  C  S  K  C  K  G
1709  tagttttgtttgcccttaccagttaatcgaatcatttttatttaaaataactttggttga
1769  gcgttcttttgtctttttttcagCAAGGGCTCGAAGTCTGGTGCCTCAATGAGGTGCCCT
                             K  G  S  K  S  G  A  S  M  R  C  P
1829  GGTTGCCAGGGCTCAGGCATGAAAGTCACTATTCGTCAGCTGGGCCCTTCCATGATACAG
      G  C  Q  G  S  G  M  K  V  T  I  R  Q  L  G  P  S  M  I  Q
1889  CAGATGCAGCAGCCTTGCAATGAGTGCAAGGGGACTGGAGAGAGCATCAATGAGAAGGAC
      Q  M  Q  Q  P  C  N  E  C  K  G  T  G  E  S  I  N  E  K  D
1949  CGCTGTCCAGGGTGCAAGGGTGAGAAGGTCATTCAAGAGAAGAAGGTTCTTGAGGTTCAT
      R  C  P  G  C  K  G  E  K  V  I  Q  E  K  K  V  L  E  V  H
2009  GTTGAGAAGGGGATGCAACACAACCAGAACATCACCTTCCCTGGTGAAGCTGATGAAGCG
      V  E  K  G  M  Q  H  N  Q  K  I  T  F  P  G  E  A  D  E  A
2069  gtatgcttgtttaagcatcggtgtgataagatgtagaggttacttttttatgatttgaaa
2129  attattctgatgtgttatgttactcgcagCCTGATACTGTCACTGGAGACATTGTATTCG
                                   P  D  T  V  T  G  D  I  V  F  V
2189  TCCTCCAGCAGAAGGATCACTCCAAATTCAAAAGAAAGGGTGAAGATCTCTTCTATGAGC
      L  Q  Q  K  D  H  S  K  F  K  R  K  G  E  D  L  F  Y  E  H
2249  ACACCTTGTCTCTGACCGAAGCACTATGTGGGTTCCAATTTGTTCTTACACATCTGGACA
      T  L  S  L  T  E  A  L  C  G  F  Q  F  V  L  T  H  L  D  N
2309  ACAGGCAGCTTCTCATCAAATCAGACCCTGGTGAAGTTGTTAAACCTggtaagcccccctt
      R  Q  L  L  I  K  S  D  P  G  E  V  V  K  P
2369  tttttcttatagatctcaattctcacttctgcaactgtatttgtaatccttgtctgctaa
2429  atttgagcaGACCAATTCAAGGCGATTAATGATGAGGGGATGCCAATTTACCAGAGGCCT
               D  Q  F  K  A  I  N  D  E  G  M  P  I  Y  Q  R  P
2489  TTCATGAAGGGGAAGCTGTACATCCATTTCACGGTGGAGTTCCCTGACTCGTTGGCACCA
      F  M  K  G  K  L  Y  I  H  F  T  V  E  F  P  D  S  L  A  P
2549  GAGCAGTGCAAGGCTCTCGAGACAGTACTTCCACCAAGGCCTTCATCCAAGCTGACAGAC
      E  Q  C  K  A  L  E  T  V  L  P  P  R  P  S  S  K  L  T  D
2609  ATGGAGATAGATGAATGCGAGGAGACGACTATGCATGATGTGAACAACATCGAGGAAGAG
      M  E  I  D  E  C  E  E  T  T  M  H  D  V  N  N  I  E  E  E
2669  ATGCGCAGGAAGCAAGCTCACGCTGCCCAGGAGGCGTACGAGGAGGACGACGAGATGCCG
      M  R  R  K  Q  A  H  A  A  Q  E  A  Y  E  E  D  D  E  M  P
2729  GGCGGAGCCCAGAGAGTGCAGTGCGCGCAACAGTAAGCAGACTATCATCAAGGCAATTGG
      G  G  A  Q  R  V  Q  C  A  Q  Q  ***
2789  GAGGGGTGGTGCCCTTAAAGCATGGGAGTGATCTCTGGTTTTGCTGTCGCCGAGCTGGGA
2849  AATAGGAAGCTGAATCGACCTCGCAAGCGGGGAATGTATCCTTTTTTGCTGCAACATAAA
2909  AAATGCTACCCAGGCATAGCTGGGTACC
```

FIG. 2B

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 832 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GGGTTTGAGC   TCAAGCCGCA   ACAACAAATT   TCGGTGCTCC   CAAGCTTCAT   AAAGGCTATC        60

TTCGGCGTCG   TTGGGATCCA   TGGTGGCACA   GAATCGAGTT   GATGTTGTAG   CTGGCGGCTA       120

GGGTTTGAAG   TGGAGAAGAG   GTCCGGCTGG   TGGCATCCTA   TCGTCTATTG   AGGGTTGGGT       180

CCGGTGGCAT   CATACTTGAT   GACAATTGAA   AGTAATTTTA   ATCAACTTGT   CATGAGTAGT       240

GAGTCTTTTA   TAAAAAATAA   GCTGAAATAA   GCACCCTTTG   ATGAGCTTAT   AGGATTATCA       300
```

-continued

| | | | | | |
|---|---|---|---|---|---|
| TAATCTCAAA | TGCTAAATTA | TATAATTTTA | TTAGATAAGT | TGCTTGTTTG | TTTCCCCACT | 360 |
| AGCTTATTTA | CATTGGATTA | TATAATCTAC | ATAAATTATA | ATCTCAAACA | AAAAGTCCTT | 420 |
| AATCAGAGAT | CAGCGAGGTC | TCACGAGTGA | GAAGGCGAGA | GCTTGTCCAA | ACGAGCATTT | 480 |
| TCGGGCGTGT | GAACACCCAT | TTCAGCAAAG | CCGTCGTTGT | CCAGTTCAGC | GAAGCGCATT | 540 |
| CTGCGGCTTT | GGCGTGACCC | ATTCTGCTAG | CTCAGCACTG | AGAATACGCG | TCCGCTGCAG | 600 |
| CGTTGGCGTA | CAGGCCGGAC | TACATTAGCC | AACGCGTATC | GGCAGTGGCA | AACCTCTTCG | 660 |
| CTTCTAACTC | CGCTGGGCCA | CCAGCTTGA | CCGCCGCCTC | CCTTCCCCTC | CGCTACTGCT | 720 |
| CCTCCCCACC | CCACTCCCCC | GCAGGAGCGG | CGGCGGCGGC | GGCGAGGTCG | TACCCCACAT | 780 |
| CGGCGAGCGG | CGGCGGCACC | GCCGGAGGCA | AAGGCAAGTC | TAGATCTAAC | CC | 832 |

(2) INFORMATION FOR SEQ ID NO:2:

(i) SEQUENCE CHARACTERISTICS:
(A) LENGTH: 3748 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: join(813..962, 2120..2284, 2376..2519,
2605..2880, 2970..3167, 3250..3573)

(xi) SEQUENCE DESCRIPTION: SEQ ID NO:2:

| | | | | | |
|---|---|---|---|---|---|
| GAGCTCAAGC | CGCAACAACA | AATTTCGGTG | CTCCCAAGCT | TCATAAAGGC | TATCTTCGGC | 60 |
| GTCGTTGGGA | TCCATGGTGG | CACAGAATCG | AGTTGATGTT | GTAGCTGGCG | GCTAGGGTTT | 120 |
| GAAGTGGAGA | AGAGGTCCGG | CTGGTGGCAT | CCTATCGTCT | ATTGAGGGTT | GGGTCCGGTG | 180 |
| GCATCATACT | TGATGACAAT | TGAAAGTAAT | TTTAATCAAC | TTGTCATGAG | TAGTGAGTCT | 240 |
| TTTATAAAAA | ATAAGCTGAA | ATAAGCACCC | TTTGATGAGC | TTATAGGATT | ATCATAATCT | 300 |
| CAAATGCTAA | ATTATATAAT | TTTATTAGAT | AAGTTGCTTG | TTTGTTTCCC | CACTAGCTTA | 360 |
| TTTACATTGG | ATTATATAAT | CTACATAAAT | TATAATCTCA | ACAAAAAGT | CCTTAATCAG | 420 |
| AGATCAGCGA | GGTCTCACGA | GTGAGAAGGC | GAGAGCTTGT | CCAAACGAGC | ATTTCGGGC | 480 |
| GTGTGAACAC | CCATTTCAGC | AAAGCCGTCG | TTGTCCAGTT | CAGCGAAGCG | CATTCTGCGG | 540 |
| CTTTGGCGTG | ACCCATTCTG | CTAGCTCAGC | ACTGAGAATA | CGCGTCCGCT | GCAGCGTTGG | 600 |
| CGTACAGGCC | GGACTACATT | AGCCAACGCG | TATCGGCAGT | GGCAAACCTC | TTCGCTTCTA | 660 |
| ACTCCGCTGG | GCCACCAGCT | TTGACCGCCG | CCTCCCTTCC | CCTCCGCTAC | TGCTCCTCCC | 720 |
| CACCCCACTC | CCCCGCAGGA | GCGGCGGCGG | CGGCGGCGAG | GTCGTACCCC | ACATCGGCGA | 780 |

| | | | | | | | | | | |
|---|---|---|---|---|---|---|---|---|---|---|
| GCGGCGGCGG | CACCGCCGGA | GGCAAAGGCA | AG | ATG | TTC | GGG | CGC | GCG | CCG | AAG | 833 |
| | | | | Met | Phe | Gly | Arg | Ala | Pro | Lys | |
| | | | | 1 | | | | 5 | | | |

| | | | | | | | | | | |
|---|---|---|---|---|---|---|---|---|---|---|
| AAG | AGC | GAC | AAC | ACC | AAG | TAC | TAC | GAG | ATC | CTC | GGG | GTG | CCC | AAG | TCG | 881 |
| Lys | Ser | Asp | Asn | Thr | Lys | Tyr | Tyr | Glu | Ile | Leu | Gly | Val | Pro | Lys | Ser | |
| | 10 | | | | | 15 | | | | | 20 | | | | | |

| | | | | | | | | | | |
|---|---|---|---|---|---|---|---|---|---|---|
| GCG | TCC | CAG | GAC | GAT | CTC | AAG | AAG | GCC | TAC | CGC | AAG | GCT | GCT | ATC | AAG | 929 |
| Ala | Ser | Gln | Asp | Asp | Leu | Lys | Lys | Ala | Tyr | Arg | Lys | Ala | Ala | Ile | Lys | |
| | 25 | | | | 30 | | | | | 35 | | | | | | |

| | | | | | | | | | | |
|---|---|---|---|---|---|---|---|---|---|---|
| AAC | CAC | CCC | GAC | AAG | GGC | GGT | GAC | CCC | GAG | AAG | GTCCGGACCA | CCCCCTCTCC | 982 |
| Asn | His | Pro | Asp | Lys | Gly | Gly | Asp | Pro | Glu | Lys | | | |
| 40 | | | | 45 | | | | | 50 | | | | |

| | | | | | |
|---|---|---|---|---|---|
| CCTCTTGCGA | TCTGGCCTTG | ATCCGATCTG | GCGTGATCCG | TTGCGGTAGA | TCGAGGTTCT | 1042 |

-continued

```
CGGCAGCCTT CGCGTCTGGT AGATTTACCT CAGGAAGGGT TGCATGTTGG TCTTGATGTT      1102
TAGGTTTGGA TTCCTCGTCC TCGGTAGATT CGTTGATGCT TCTGTAGGTA ACAAGCCGCG      1162
ATTGGTAGTT CCTGTTGCAT GCGCTGGTTT GTGGTGGTCG ATTCGCGGTC ATGTGTACCA      1222
TGATTGCGAC CTTAGTTGCG TAGGGGATTC GCGAGAACCA TCTCCGTGTG CTTGCTGCGG      1282
TCAGAATCCT AAGCAGGTGA AACCGAACAG TTTTTAGCT  TGCATGCCAT GTGCGGTTCT      1342
CGCGGTCATG TGTTATGAAC TTGTGATTCA CCTCGCACAT GTATATTGGC TAGTATTTCT      1402
TTTTCGATGA CAGGCAACGA CGCAACGTCG CAGCTGGCTC AGGTGCAAAC ATTTGTAGTT      1462
GGGGGTTTTC ATCGATTTTT TAGTAGTGCC TGCATTGTTC ATTTGTGCT  GCAGGTTGCT      1522
CAGTTACATG GTAACCAAGA TGCATGGTGG TTATAATTCA TTTCTCCAGA TATTTATTAC      1582
TCTAATGGTT GTGTTATATA ATCATGGCCT CATGGGAAGC CTATCCTTGT CACCTTGTTT      1642
CAGCAAGGTA TCTGTGGTCA TCCAGGAGCT GTTCAATATC TGTTTGCTTT ACCTTGATTG      1702
CCCTTTTGTA TGTTCCTAGG CTTTTCTGT  CTGTTATGTA GCATATTGTG TGTTTTCTTA      1762
TCTTGTGAAG CTTAGAAGGT TTGCTTGTTT GGTATAATCA CCTGGAGATC ATTGGCTGTA      1822
TTCCTTTTGT ATTAAAACTC GTGTTTTTT  TTTTGCAGAT GTTACATGTG TTTCCACCAC      1882
ATTATTTGAG CCAGTAATAT TGTTTTGCA  GGCTATATGA TTGTTCTATT TCTTGCTTAT      1942
TTTGTATACC ATAATAGTGC TGCTATATAC AATGATGATT TTGTTTAATA AAAAAACATA      2002
TATAGAAGTG ACGGATGTAA AGATATATGT TCTCTTCAAC TAGTTCAGTC TGTCAGCTAA      2062
ATTTCTTTTT TGATTCATGA TTTGTAGAGT AAAATCTTTA TTTTTAATTT ATTTCAG        2119

TTC AAG GAG CTC GCA CAA GCC TAT GAG GTT TTG AGT GAT CCA GAG AAA       2167
Phe Lys Glu Leu Ala Gln Ala Tyr Glu Val Leu Ser Asp Pro Glu Lys
             55                  60                  65

CGT GAG ATT TAT GAT CAG TAT GGT GAA GAT GCC CTT AAG GAA GGA ATG       2215
Arg Glu Ile Tyr Asp Gln Tyr Gly Glu Asp Ala Leu Lys Glu Gly Met
         70                  75                  80

GGC GGT GGA GGA TCC CAT GTT GAT CCA TTT GAC ATC TTC TCA TCA TTT       2263
Gly Gly Gly Gly Ser His Val Asp Pro Phe Asp Ile Phe Ser Ser Phe
     85                  90                  95

TTT GGA CCC TCT TTT GGA GGT ATTGTACCCA TATTCATTTG TGACTGTTTT          2314
Phe Gly Pro Ser Phe Gly Gly
100                 105

TTTGGTACGC TCCTTTATCA AATGTGATAA TGACTGGCTT TTATTTGTTT TATTTGCAGG     2374

A GGT GGT GGA AGC AGC AGG GGA AGA AGG CAA AGG AGG GGA GAA GAT         2420
  Gly Gly Gly Ser Ser Arg Gly Arg Arg Gln Arg Arg Gly Glu Asp
              110                 115                 120

GTA GTT CAC CCA CTT AAA GTT TCT CTG GAA GAT CTT TAC AAT GGC ACC       2468
Val Val His Pro Leu Lys Val Ser Leu Glu Asp Leu Tyr Asn Gly Thr
              125                 130                 135

TCA AAG AAG CTC TCT CTT TCG CGC AAT GTC ATC TGC TCC AAG TGC AAG       2516
Ser Lys Lys Leu Ser Leu Ser Arg Asn Val Ile Cys Ser Lys Cys Lys
         140                 145                 150

GGG TTAGTTTTGT TTGCCCTTAC CAGTTAATCG AATCATTTTA TTTTAAAATA            2569
Gly

ACTTTGGTTG AGCGTTCTTT TGTCTTTTTT TCAGC AAG GGC TCG AAG TCT GGT        2622
                                       Lys Gly Ser Lys Ser Gly
                                                   155

GCC TCA ATG AGG TGC CCT GGT TGC CAG GGC TCA GGC ATG AAA GTC ACT       2670
Ala Ser Met Arg Cys Pro Gly Cys Gln Gly Ser Gly Met Lys Val Thr
160                 165                 170                 175

ATT CGT CAG CTG GGC CCT TCC ATG ATA CAG CAG ATG CAG CAG CCT TGC       2718
Ile Arg Gln Leu Gly Pro Ser Met Ile Gln Gln Met Gln Gln Pro Cys
```

|  |  |  |  |  |  |  |  |  |  |  |  |  |  |  |  |
|---|---|---|---|---|---|---|---|---|---|---|---|---|---|---|---|
|  |  |  |  | 180 |  |  |  |  | 185 |  |  |  |  | 190 |  |
| AAT | GAG | TGC | AAG | GGG | ACT | GGA | GAG | AGC | ATC | AAT | GAG | AAG | GAC | CGC | TGT |
| Asn | Glu | Cys | Lys | Gly | Thr | Gly | Glu | Ser | Ile | Asn | Glu | Lys | Asp | Arg | Cys |
|  |  |  | 195 |  |  |  |  | 200 |  |  |  | 205 |  |  |  |

2766

| CCA | GGG | TGC | AAG | GGT | GAG | AAG | GTC | ATT | CAA | GAG | AAG | AAG | GTT | CTT | GAG |
|---|---|---|---|---|---|---|---|---|---|---|---|---|---|---|---|
| Pro | Gly | Cys | Lys | Gly | Glu | Lys | Val | Ile | Gln | Glu | Lys | Lys | Val | Leu | Glu |
|  |  |  | 210 |  |  |  |  | 215 |  |  |  | 220 |  |  |  |

2814

| GTT | CAT | GTT | GAG | AAG | GGG | ATG | CAA | CAC | AAC | CAG | AAG | ATC | ACC | TTC | CCT |
|---|---|---|---|---|---|---|---|---|---|---|---|---|---|---|---|
| Val | His | Val | Glu | Lys | Gly | Met | Gln | His | Asn | Gln | Lys | Ile | Thr | Phe | Pro |
|  |  | 225 |  |  |  |  | 230 |  |  |  |  | 235 |  |  |  |

2862

| GGT | GAA | GCT | GAT | GAA | GCG | GTATGCTTGT | TTAAGCATCG | GTGTGATAAG |
|---|---|---|---|---|---|---|---|---|
| Gly | Glu | Ala | Asp | Glu | Ala |  |  |  |
| 240 |  |  |  |  | 245 |  |  |  |

2910

ATGTAGAGGT TACTTTTTTA TGATTTGAAA ATTATTCTGA TGTGTTATGT TACTCGCAG  2969

| CCT | GAT | ACT | GTC | ACT | GGA | GAC | ATT | GTA | TTC | GTC | CTC | CAG | CAG | AAG | GAT |
|---|---|---|---|---|---|---|---|---|---|---|---|---|---|---|---|
| Pro | Asp | Thr | Val | Thr | Gly | Asp | Ile | Val | Phe | Val | Leu | Gln | Gln | Lys | Asp |
|  |  |  |  | 250 |  |  |  |  | 255 |  |  |  |  | 260 |  |

3017

| CAC | TCC | AAA | TTC | AAA | AGA | AAG | GGT | GAA | GAT | CTC | TTC | TAT | GAG | CAC | ACC |
|---|---|---|---|---|---|---|---|---|---|---|---|---|---|---|---|
| His | Ser | Lys | Phe | Lys | Arg | Lys | Gly | Glu | Asp | Leu | Phe | Tyr | Glu | His | Thr |
|  |  |  | 265 |  |  |  |  | 270 |  |  |  | 275 |  |  |  |

3065

| TTG | TCT | CTG | ACC | GAA | GCA | CTA | TGT | GGG | TTC | CAA | TTT | GTT | CTT | ACA | CAT |
|---|---|---|---|---|---|---|---|---|---|---|---|---|---|---|---|
| Leu | Ser | Leu | Thr | Glu | Ala | Leu | Cys | Gly | Phe | Gln | Phe | Val | Leu | Thr | His |
|  |  |  | 280 |  |  |  |  | 285 |  |  |  | 290 |  |  |  |

3113

| CTG | GAC | AAC | AGG | CAG | CTT | CTC | ATC | AAA | TCA | GAC | CCT | GGT | GAA | GTT | GTT |
|---|---|---|---|---|---|---|---|---|---|---|---|---|---|---|---|
| Leu | Asp | Asn | Arg | Gln | Leu | Leu | Ile | Lys | Ser | Asp | Pro | Gly | Glu | Val | Val |
|  |  | 295 |  |  |  |  | 300 |  |  |  |  | 305 |  |  |  |

3161

| AAA | CCT | GGTAAGCCCC | CTTTTTTTCT | TATAGATCTC | AATTCTCACT | TCTGCAACTG |
|---|---|---|---|---|---|---|
| Lys | Pro |  |  |  |  |  |
| 310 |  |  |  |  |  |  |

3217

| TATTTGTAAT | CCTTGTCTGC | TAAATTTGAG | CA | GAC | CAA | TTC | AAG | GCG | ATT | AAT |
|---|---|---|---|---|---|---|---|---|---|---|
|  |  |  |  | Asp | Gln | Phe | Lys | Ala | Ile | Asn |
|  |  |  |  |  |  |  | 315 |  |  |  |

3270

| GAT | GAG | GGG | ATG | CCA | ATT | TAC | CAG | AGG | CCT | TTC | ATG | AAG | GGG | AAG | CTG |
|---|---|---|---|---|---|---|---|---|---|---|---|---|---|---|---|
| Asp | Glu | Gly | Met | Pro | Ile | Tyr | Gln | Arg | Pro | Phe | Met | Lys | Gly | Lys | Leu |
|  | 320 |  |  |  |  | 325 |  |  |  |  | 330 |  |  |  |  |

3318

| TAC | ATC | CAT | TTC | ACG | GTG | GAG | TTC | CCT | GAC | TCG | TTG | GCA | CCA | GAG | CAG |
|---|---|---|---|---|---|---|---|---|---|---|---|---|---|---|---|
| Tyr | Ile | His | Phe | Thr | Val | Glu | Phe | Pro | Asp | Ser | Leu | Ala | Pro | Glu | Gln |
| 335 |  |  |  | 340 |  |  |  |  | 345 |  |  |  |  |  | 350 |

3366

| TGC | AAG | GCT | CTC | GAG | ACA | GTA | CTT | CCA | CCA | AGG | CCT | TCA | TCC | AAG | CTG |
|---|---|---|---|---|---|---|---|---|---|---|---|---|---|---|---|
| Cys | Lys | Ala | Leu | Glu | Thr | Val | Leu | Pro | Pro | Arg | Pro | Ser | Ser | Lys | Leu |
|  |  |  |  | 355 |  |  |  |  | 360 |  |  |  |  | 365 |  |

3414

| ACA | GAC | ATG | GAG | ATA | GAT | GAA | TGC | GAG | GAG | ACG | ACT | ATG | CAT | GAT | GTG |
|---|---|---|---|---|---|---|---|---|---|---|---|---|---|---|---|
| Thr | Asp | Met | Glu | Ile | Asp | Glu | Cys | Glu | Glu | Thr | Thr | Met | His | Asp | Val |
|  |  |  | 370 |  |  |  |  | 375 |  |  |  |  | 380 |  |  |

3462

| AAC | AAC | ATC | GAG | GAA | GAG | ATG | CGC | AGG | AAG | CAA | GCT | CAC | GCT | GCC | CAG |
|---|---|---|---|---|---|---|---|---|---|---|---|---|---|---|---|
| Asn | Asn | Ile | Glu | Glu | Glu | Met | Arg | Arg | Lys | Gln | Ala | His | Ala | Ala | Gln |
|  |  | 385 |  |  |  |  | 390 |  |  |  |  | 395 |  |  |  |

3510

| GAG | GCG | TAC | GAG | GAG | GAC | GAC | GAG | ATG | CCG | GGC | GGA | GCC | CAG | AGA | GTG |
|---|---|---|---|---|---|---|---|---|---|---|---|---|---|---|---|
| Glu | Ala | Tyr | Glu | Glu | Asp | Asp | Glu | Met | Pro | Gly | Gly | Ala | Gln | Arg | Val |
|  | 400 |  |  |  |  | 405 |  |  |  |  | 410 |  |  |  |  |

3558

| CAG | TGC | GCG | CAA | CAG | TAAGCAGACT | ATCATCAAGG | CAATTGGGAG | GGGTGGTGCC |
|---|---|---|---|---|---|---|---|---|
| Gln | Cys | Ala | Gln | Gln |  |  |  |  |
| 415 |  |  |  |  |  |  |  |  |

3613

CTTAAAGCAT GGGAGTGATC TCTGGTTTTG CTGTCGCCGA GCTGGGAAAT AGGAAGCTGA  3673

ATCGACCTCG CAAGCGGGGA ATGTATCCTT TTTTGCTGCA ACATAAAAAA TGCTACCCAG  3733

GCATAGCTGG GTACC  3748

( 2 ) INFORMATION FOR SEQ ID NO:3:

(i) SEQUENCE CHARACTERISTICS:
  (A) LENGTH: 419 amino acids
  (B) TYPE: amino acid
  (D) TOPOLOGY: linear (ii) MOLECULE TYPE: protein (xi) SEQUENCE DESCRIPTION: SEQ ID NO:3:

```
Met Phe Gly Arg Ala Pro Lys Lys Ser Asp Asn Thr Lys Tyr Tyr Glu
  1               5                  10                  15
Ile Leu Gly Val Pro Lys Ser Ala Ser Gln Asp Asp Leu Lys Lys Ala
                 20                  25                  30
Tyr Arg Lys Ala Ala Ile Lys Asn His Pro Asp Lys Gly Gly Asp Pro
             35                  40                  45
Glu Lys Phe Lys Glu Leu Ala Gln Ala Tyr Glu Val Leu Ser Asp Pro
         50                  55                  60
Glu Lys Arg Glu Ile Tyr Asp Gln Tyr Gly Glu Asp Ala Leu Lys Glu
 65                  70                  75                  80
Gly Met Gly Gly Gly Gly Ser His Val Asp Pro Phe Asp Ile Phe Ser
                     85                  90                  95
Ser Phe Phe Gly Pro Ser Phe Gly Gly Gly Gly Ser Ser Arg Gly
                100                 105                 110
Arg Arg Gln Arg Arg Gly Glu Asp Val Val His Pro Leu Lys Val Ser
             115                 120                 125
Leu Glu Asp Leu Tyr Asn Gly Thr Ser Lys Lys Leu Ser Leu Ser Arg
 130                 135                 140
Asn Val Ile Cys Ser Lys Cys Lys Gly Lys Gly Ser Lys Ser Gly Ala
 145                 150                 155                 160
Ser Met Arg Cys Pro Gly Cys Gln Gly Ser Gly Met Lys Val Thr Ile
                 165                 170                 175
Arg Gln Leu Gly Pro Ser Met Ile Gln Gln Met Gln Gln Pro Cys Asn
             180                 185                 190
Glu Cys Lys Gly Thr Gly Glu Ser Ile Asn Glu Lys Asp Arg Cys Pro
         195                 200                 205
Gly Cys Lys Gly Glu Lys Val Ile Gln Glu Lys Lys Val Leu Glu Val
 210                 215                 220
His Val Glu Lys Gly Met Gln His Asn Gln Lys Ile Thr Phe Pro Gly
 225                 230                 235                 240
Glu Ala Asp Glu Ala Pro Asp Thr Val Thr Gly Asp Ile Val Phe Val
             245                 250                 255
Leu Gln Gln Lys Asp His Ser Lys Phe Lys Arg Lys Gly Glu Asp Leu
         260                 265                 270
Phe Tyr Glu His Thr Leu Ser Leu Thr Glu Ala Leu Cys Gly Phe Gln
     275                 280                 285
Phe Val Leu Thr His Leu Asp Asn Arg Gln Leu Leu Ile Lys Ser Asp
 290                 295                 300
Pro Gly Glu Val Val Lys Pro Asp Gln Phe Lys Ala Ile Asn Asp Glu
 305                 310                 315                 320
Gly Met Pro Ile Tyr Gln Arg Pro Phe Met Lys Gly Lys Leu Tyr Ile
             325                 330                 335
His Phe Thr Val Glu Phe Pro Asp Ser Leu Ala Pro Glu Gln Cys Lys
         340                 345                 350
Ala Leu Glu Thr Val Leu Pro Pro Arg Pro Ser Ser Lys Leu Thr Asp
     355                 360                 365
Met Glu Ile Asp Glu Cys Glu Glu Thr Thr Met His Asp Val Asn Asn
```

```
                370                             375                           380
Ile  Glu  Glu  Glu  Met  Arg  Arg  Lys  Gln  Ala  His  Ala  Ala  Gln  Glu  Ala
385                           390                         395                           400

Tyr  Glu  Glu  Asp  Asp  Glu  Met  Pro  Gly  Gly  Ala  Gln  Arg  Val  Gln  Cys
                    405                           410                         415

Ala  Gln  Gln
```

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGGTTTGAGC  TCAAGCCGCA  ACAACAAAT                      29

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGGTTAGATC  TAGACTTGCC  TTTGCCTCCG  GCGGT            35

EXPRESSION CONTROL SEQUENCE FOR GENERAL AND EFFECTIVE EXPRESSION OF GENES IN PLANTS

This application claims the benefit of U.S. Provisional Application No. 60/001,552, filed Jul. 27, 1995.

FIELD OF THE INVENTION

The invention relates to recombinant systems for creating transgenic plants that produce proteins beneficial to the plant or which are otherwise of interest. More particularly, the invention concerns expression under the control of maize control sequences which are tissue-general.

BACKGROUND ART

The transformation of plants to provide desired characteristics has been practiced for some time. Of particular interest are transgenic insect-resistant plants which have this characteristic due to their ability to produce insecticidal proteins, such as that from *B. thuringiensis*. Recombinant systems for plant transformation have thus been developed involving a variety of promoters, both constitutive (or non tissue-specific) and those which are active only in certain tissues. Notably, the CaMV 35S promoter (Odell, J. T. et al. *Nature* (1985) 313:810–812); and the Agrobacterium nopaline synthase promoter (Depicker, A. et al., *J Mol Appl Genet* (1982) 1:561–573; An, G. *Plant Physiol* (1988) 88:547–552) are among the best known, as well as the maize ubiquitin promoter described by Christensen, A. H. et al. *Plant Mol Bio.* (1992) 18:675–689. Additionally, promoters which are green tissue preferred, such as PEP carboxylase (Hudspeth, R. L. and Grula, J. W. *Plant Mol Biol* (1989) 12:579–589) and pollen-specific promoters (Guerrero, F. D. et al. *Mol Gen Genet* (1990) 224:161–168, Twell, D. et al. *Genes & Development* (1991) 5:496–507, Albani, D. et al. *The Plant J* (1992) 2:331–342) are also known.

It is desirable in creating transgenic plants to be able to take advantage of the availability of more than a single promoter if more than a single protein is to be produced in the modified plant. The use of common regulatory sequences driving expression of multiple genes can result in homologous recombination between the various expression systems, the formation of hairpin loops caused by two copies of the same sequence in opposite orientation in close proximity, competition between the various expression systems for binding of promoter-specific regulatory factors, and inappropriateness of the strength of expression level with respect to each of the proteins desired. For all these reasons, it would be desirable to have a repertoire of regulatory sequences operable in plants having a range of strength and a range of tissue specificities.

The present invention provides an additional member of this repertoire—the transcription/translation control sequence putatively associated with the DnaJ or DnaJ-related protein genes in maize, designated the ZMDJ1 promoter/leader sequence herein.

Thus, the promoter of the present invention is associated with a coding sequence showing homology to the published sequences of DnaJ or DnaJ-related protein genes in bacteria (Bardwell, J.C.A. et al. *J Biol Chem* (1986) 261:1782–1785; Anzola, J. et al. *Infection and Immunity* (1992) 60:4965–4968; Narberhaus, F. et al. *J Bacteriol* (1992) 174:3290–3299; van Asseldonk, M. et al. *J Bacteriol* (1993) 175:1637–1644); from yeast (Caplan, A. J. et al. *J Cell Biol* (1991) 114:609–621; and Atencio, D. P. et al. *Mol Cellul Biol* (1992) 12:283–291); and those obtained from plants (Bessoule, J.-J. *FEBS Lett* (1993) 323:51–54; Bessoule, J.-J. et al. *Plant Physiol Biochem* (1994) 32:723–727; Preisig-Müller, R. et al. *Arch Biochem Biophys* (1993) 305:30–37; and Zhu, J.-K. et al. *The Plant Cell* (1993) 5:341–349). The function of these proteins in bacteria is evidently to assist in chaperone-mediated protein folding as well as to provide cell viability at high temperatures; they are also involved in DNA replication, translation and peptide translocation across intracellular membranes. Thus, DnaJ appears important in basic cellular functions and would be expected to have a wide tissue range of effectiveness; the ZMDJ1 promoter will therefore have a characteristic tissue specificity profile.

DISCLOSURE OF THE INVENTION

The invention provides an additional member of the repertoire of control sequences which can be used to effect the expression of foreign genes in transgenic plants. The tissue specificity of this promoter appears to fall between the strictly constitutive CaMV and nopaline promoters and the highly tissue specific pollen promoter. Additionally, based upon our own and others' unpublished observations, the CaMV promoter does not express uniformly in all tissues of some plants including maize, and expresses poorly in some tissues.

In one aspect, the invention relates to an isolated and purified or recombinant DNA molecule containing a nucleotide sequence representing the ZmDJ1 control sequence of the invention, shown as positions −812 to −1 in FIG. 1, and the transcriptional and translational-related sub-sequences, thereof. This control sequence, or, generically, promoter, includes both sequences that control transcription and additional sequence corresponding to any mRNA leader upstream of the ATG (AUG) translation start codon shown in FIG. 2.

In other aspects, the invention relates to expression systems containing these control sequences operably linked to a coding sequence so as to effect the expression of the coding sequence in plant cells or in transgenic plants. In still another aspect, the invention relates to plant cells, plant parts and plants modified to contain an expression system for a protein heterologous to the cell, part or plant in which expression is under the control of the ZMDJ1 control sequences. In still other aspects, the invention is directed to methods to transform plant cells, plant parts or plants to provide a desired property, such methods comprising modifying the cell, part or plant to contain the expression system of the invention.

In still other aspects, the invention relates to antisense and triple-helix forming constructs useful to control expression levels.

BRIEF DESCRIPTION OF THE DRAWINGS

FIG. 1 (SEQ ID NO: 1 shows the nucleotide sequence of the control sequence of the invention.

FIG. 2 (SEQ ID NO: 2 and SEQ ID NO: 3 shows the nucleotide sequence of a maize genomic clone containing the control sequence of the invention and a downstream coding region.

MODES OF CARRYING OUT THE INVENTION

Figure 3:
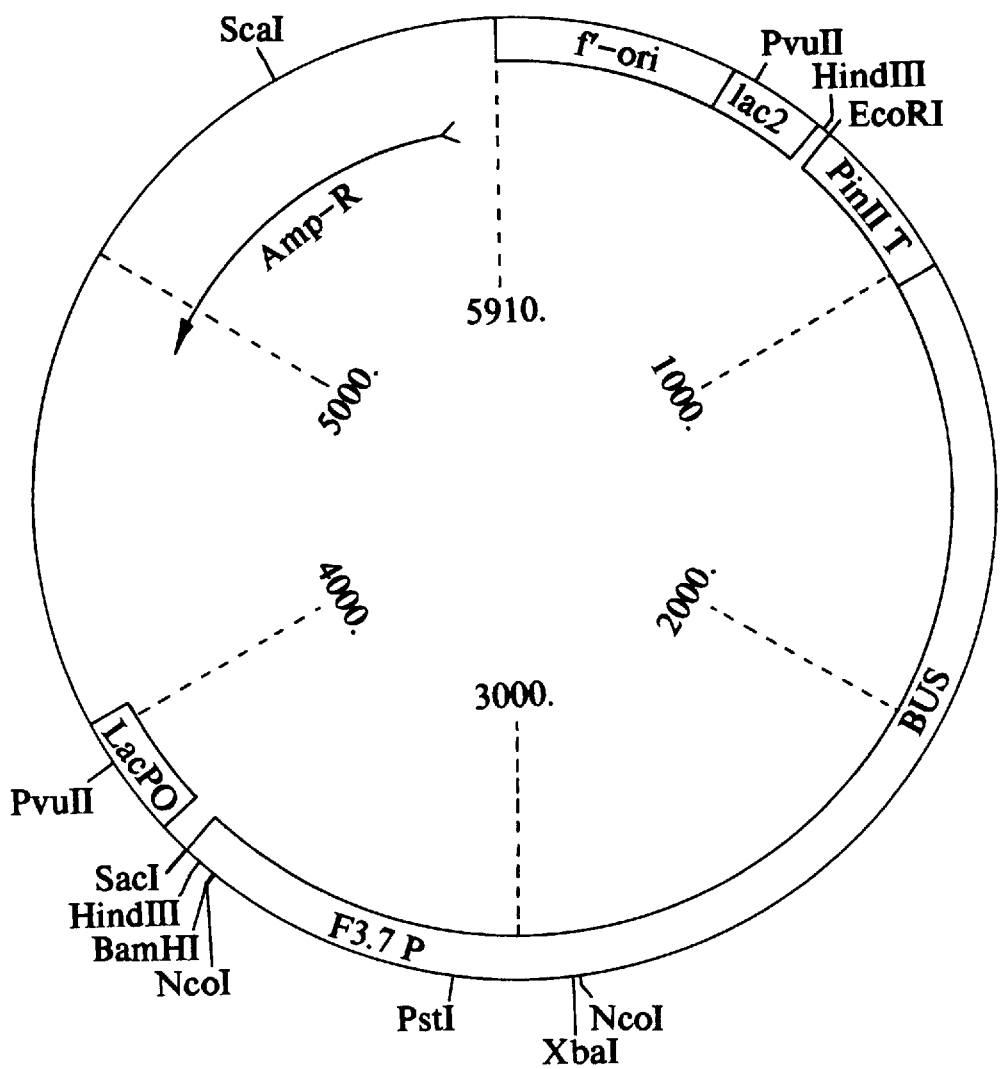
FIG. 3 is a diagram of pPH15897.

The invention provides an additional promoter and leader sequence with a unique tissue-specificity profile and characteristic transcription strength which is useful in the modification of plants or their cells or parts to enable them to produce foreign proteins. The control sequence has the nucleotide sequence set forth as positions −812 to −1 in FIG. 1. The −1 position of FIG. 1 is immediately upstream of the ATG translation start codon shown in FIG. 2. Thus, the control sequence, sometimes referred to as a "promoter" herein, includes both the transcriptional promoter and intervening sequences relevant to translation, including those corresponding to untranslated upstream mRNA. This set of expression control sequences is constitutive in that it is capable of effecting expression of operably linked coding sequences in a variety of plant tissues including eleven week old leaf blade, leaf whorl, leaf collar, stalk rind, stalk pith, stalk node, roots and kernels. It is particularly useful in a preferred embodiment to control *Ostrinia nubilalis* or the European corn borer (ECB) in maize. Previous work has utilized the *Bacillus thuringiensis* cryA(b) gene under control of the CaMV 35S promoter as well as this gene under control of the maize PEP carboxylase promoter and the pollen promoter as described by Koziel, M. G. et al. *Bio/Technol* (1993) 11:194–200.

Manipulation of the ZmDJ1 Control Sequence

The recovery of the ZmDJ1 control sequence is described in detail hereinbelow. Of course, as the complete nucleotide sequence is provided, it is unnecessary to repeat this isolation process; the nucleotide sequence can simply be constructed de novo using standard commercial equipment for solid-phase synthesis or by any other convenient method. Conventional methods for synthesizing nucleic acid molecules of this length are by now well known in the art.

The ZmDJ1 promoter of the invention, like other promoters, has inherent characteristics which determine the transcription levels that will result from its operable linkage to a desired gene sequence. The operability and strength of the promoter is controlled by transcription factors that are characteristic of particular cellular environments—and, by extrapolation, to factors characteristic of particular tissues—and may vary with the stage of development of the tissue as well. Factors that affect the translational efficiency associated with features of the leader sequence will also be variable. Therefore, although plants, which contain differentiated cells and tissues, may be modified systemically by insertion of expression systems under the control of the ZmDJ1 promoter, the transcriptional and translational efficiency of the control sequence will be determined by the cell or tissue in which it resides and by the cell or tissue stage of development.

In addition, since the nucleotide sequence of the promoter is known and since techniques are readily available to vary the nucleotide sequence at will, minor modifications can be made in the sequence to alter the profile of expression as dependent on tissue location and stage of development. As the literature develops, short sequences that influence tissue specificity become known, and modifications can be made according to these.

The control sequence region has been defined as the sequence between positions −812 to −1 upstream of the translation site, as further described below. However, the entire sequence may not be necessary to promote expression of the operably linked genes effectively. It is clear, for example, that this nucleotide sequence contains both a transcriptional promoter and a portion corresponding to an upstream "leader" sequence transcribed into the intermediate mRNA immediately upstream of the translation start codon. Thus, the transcriptional promoter could be used to effect expression independently of the homologous leader; similarly, the leader sequence could be used in combination with a heterologous promoter. Accordingly, fragments of the control sequence which retain transcription-initiating activity and/or the function of the leader sequence can also be used and are included within the definition of ZmDJ1 control sequence. Furthermore, there may be a requirement only for portions of the transcriptional promoter and/or leader sequence. The effectiveness of such fragments can readily be tested using marker expression systems as is known in the art.

Construction of Expression Systems

An expression system can be constructed wherein a desired coding nucleotide sequence is under the control of the ZmDJ1 promoter by standard methods understood in the art. The disclosure herein provides a form of the promoter with restriction sites at either end; these restriction sites may be used directly, or modifications can be made to employ other restriction sites in the alternative. Using standard gene splicing techniques, the ZmDJ1 promoter can be ligated at an appropriate distance from the translation start locus of the gene encoding any desirable protein. The gene will include not only the coding region but the upstream and downstream untranslated regions either indigenous to the coding sequence or heterologous or partially heterologous thereto. Such variations are well understood by ordinarily skilled practitioners. The recombinant expression system will thus contain, as part of, or in addition to the desired protein-encoding sequences and the ZmDJ1 promoter, transcription and translation initiation sites, as well as transcription and translation termination sequences. Such termination sequences include, but are not limited to, the Agrobacterium octopine synthase 3' sequence (Gielen et al. *EMBO J* (1984) 3:835–846) the nopaline synthase 3' sequence (Depicker et al. *Mol and Appl Genet* (1982) 1:561–573) or the potato proteinase inhibitor II (PinII) 3' sequence (An et al. *Plant Cell* (1989) 1:115–122). Unique restriction enzyme sites at the 5' and 3' ends of the expression system are typically included to allow for easy insertion into a preexisting vector.

Suitable proteins whose production may be desired in plants include insecticidal proteins, antifungal proteins, enzymes, nutritional proteins, and proteins whose production is desired per se such as erythropoietin, human insulin, cytokines, interferons, growth hormones, gonadotropins, immunoglobulins and other proteins of pharmaceutical interest. Particularly useful are the family of cry genes of *B. thuringiensis*, including, but not limited to cryIA(b), cryIIa and others.

The ZmDJ1 control sequence is preferably positioned about the same distance from the translation start site as it is from the translation start site in its natural setting. As is known in the art, however, some variation in this distance can be accommodated without loss of promoter function.

The resulting expression system is ligated into or otherwise constructed to be included in a recombinant vector which is appropriate for higher plant transformation. The vector may also typically contain a selectable marker gene by which transformed plant cells can be identified in culture. Usually, the marker gene will encode antibiotic resistance. These markers include resistance to G418, hygromycin, bleomycin, kanamycin, neomycin and gentamicin. After transforming the plant cells, those cells having the vector will be identified by their ability to grow on a medium containing the particular antibiotic. Alternatively, the expression system containing vector, and the plant selectable marker gene containing vectors could be introduced on separate plasmids followed by identification of plant cells containing both sets of sequences.

Replication sequences of bacterial or viral origin are generally also included to allow the vector to be cloned in a bacterial or phage host, preferably a broad host range procaryotic origin of replication is included. A selectable marker for bacteria should also be included to allow selection of bacterial cells bearing the desired construct. Suitable procaryotic selectable markers also include resistance to antibiotics such as ampicillin, kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

Transformation of Plants

The expression system can be introduced into plants in a variety of ways known in the art.

All types of plants are appropriate subjects for "direct" transformation; in general, only dicots can be transformed using Agrobacterium-mediated infection, although recent progress has been made in monocot transformation using this method.

In one form of direct transformation, the vector is microinjected directly into plant cells by use of micropipettes to mechanically transfer-the recombinant DNA (Crossway *Mol Gen Genetics* (1985) 202:179–185). In another form, the genetic material is transferred into the plant cell using polyethylene glycol (Krens, et al. *Nature* (1982) 296:72–74), or high velocity ballistic penetration by small particles with the nucleic acid either within the matrix of small beads or particles, or on the surface, is used (Klein, et al. *Nature* (1987) 327:70–73). In still another method protoplasts are fused with other entities which contain the DNA whose introduction is desired. These entities are minicells, cells, lysosomes or other fusible lipid-surfaced bodies (Fraley, et al. *Proc Natl Acad Sci USA* (1982) 79:1859–1863).

DNA may also be introduced into the plant cells by electroporation (Fromm et al. *Proc Natl Acad Sci USA* (1985) 82:5824). In this technique, plant protoplasts are electroporated in the presence of plasmids containing the expression system. Electrical impulses of high field strength reversibly permeabilize biomembranes allowing the introduction of the plasmids. Electroporated plant protoplasts reform the cell wall, divide, and regenerate.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression systems. In addition, assaying for the presence of opines can be used to identify transformed tissue.

Heterologous genetic sequences can be introduced into appropriate plant cells by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J. *Science* (1987) 237:1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema et al. *Nature* (1983) 303:179–189). The transferred DNA region can be increased in size by the insertion of heterologous DNA without affecting its ability to be transferred. Thus a modified Ti or Ri plasmid, in which the tumor-inducing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes-constructed from foreign sequences. These may include but are not limited to "shuttle vectors," (Ruvkum and Ausubel *Nature* (1981) 298:85–88), promoters (Lawton et al. *Plant Mol Biol* (1987) 9:315–324) and structural genes for antibiotic resistance as a selection factor (Fraley et al. *Proc Natl Acad Sci* (1983) 80:4803–4807).

There are two classes of recombinant Ti and Ri plasmid vector systems now in use. In one class, called "cointegrate," the shuttle vector containing the gene of interest is inserted by genetic recombination into a nononcogenic Ti plasmid that contains both the cis-acting and trans-acting elements required for plant transformation as, for example, in the pMLJ1 shuttle vector of DeBlock et al. *EMBO J* (1984) 3:1681–1689 and the nononcogenic Ti plasmid pGV3850 described by Zambryski et al. *EMBO J* (1983) 2:2143–2150. In the second class or "binary" system, the gene of interest is inserted into a shuttle vector containing the cis-acting elements required for plant transformation. The other necessary functions are provided in trans by the nononcogenic Ti plasmid as exemplified by the pBIN19 shuttle vector described by Bevan, *Nucleic Acids Research* (1984) 12:8711–8721 and the nononcogenic Ti plasmid PAL4404 described by Hoekma, et al. *Nature* (1983) 303:179–180. Some of these vectors are commercially available.

There are two common ways to transform plant cells with Agrobacterium: cocultivation of Agrobacterium with cultured isolated protoplasts, or transformation of intact cells or tissues with Agrobacterium. The first requires an established culture system-that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Attempts to transform them using Agrobacterium have been unsuccessful until recently (Hooykas-Van Slogteren et al. *Nature* (1984) 311:763–764). However, there is growing evidence now that certain monocots can be transformed by Agrobacterium. Using novel experimental approaches cereal species such as rye (de la Pena et al. *Nature* (1987) 325:274–276), maize (Rhodes et al. *Science* (1988) 240:204–207), and rice (Shimamoto et al. *Nature* (1989) 338:274–276) may now be transformed.

Identification of transformed cells or plants is generally accomplished by including a selectable marker in the transforming vector, or by obtaining evidence of successful bacterial infection.

Regeneration

After insertion of the expression system plants can be regenerated by standard methods.

Plant regeneration from cultured protoplasts is described in Evans et al. *Handbook of Plant Cell Cultures,* vol. 1: (MacMillan Publishing Co. N.Y., 1983); and Vasil I. R. (ed.) *Cell Culture and Somatic Cell Genetics of Plants,* Acad. Press, Orlando, Vol. I, 1984, and Vol. II, 1986). It is known that practically all plants can be regenerated from cultured cells or tissues, including but not limited to maize, sunflower, sorghum, *Brassica sp.,* Arabidopsis, tobacco, tomato, wheat, rye, as well as all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants. After the expression system is stably incorporated into regenerated transgenic plants, it can be transferred to other plants by sexual crossing. Any of a number of standard breeding techniques can be used, depending upon the species to be crossed. The plants are grown and harvested using conventional procedures.

Control of Expression

The availability of the ZmDJ1 control sequence permits design of recombinant materials that can be used to control the expression of genes that are operably linked to the transcriptional promoter and/or leader sequence. For example, the complement to the gene sequence or to a portion thereof or an expression system capable of generating the complement in situ provide antisense constructs that can inhibit expression. If an expression system for the complement is placed under control of an inducible promoter, a secondary means to control expression is provided. The use of antisense constructs to control expression in plants, in general, is described in U.S. Pat. No. 5,107,065 incorporated herein by reference.

In addition to antisense means for controlling expression, molecules which associate with the major groove of the DNA duplex to form triple helices may also be used to control expression. Sequence-specific oligonucleotides can be designed according to known rules to provide this specific association at target sequences. The appropriate sequence rules are described in Moser, H. E., et al. *Science* (1987) 238:645–650; Cooney, M. et al. *Science* (1988) 241:456–459.

Accordingly, the invention includes antisense constructs and oligonucleotides which can effect a triple helix formation with respect to the control sequence of the invention.

The following examples are intended to illustrate but not to limit the invention.

EXAMPLE 1

Isolation of the F3.7 Promoter cDNA libraries in the lambda vector GEM-4 were constructed from mRNA isolated from 1 week old roots, 1 and 8 week old stalks, and 4 week old wounded leaf tissues of Zea mays L. (cv. B73) by standard isolation and preparation techniques. Approximately $10^6$ plaques from each library were plated and differentially screened using labeled poly $(A)^+$ mRNA from the other tissues; some plaques were identified which hybridized strongly in all of the libraries using all of the tissue RNA probes. One plaque, termed F3.7, having these characteristics was selected.

The ability of the F3.7 clone to hybridize to mRNA from a variety of tissues was confirmed. Northern analysis showed that hybridizing RNA was present in eleven week old leaf blade, leaf whorl, leaf collar, stalk rind, stalk pith, stalk node and roots as well as in maize kernels 4, 14 and 27 days post pollination. While there was some variability in band intensity, all expressing tissues following high stringency washes showed a transcript of approximately 1.5 kb.

The F3.7 cDNA clone was completely sequenced in both directions by the dideoxy chain termination method of Sanger and the resulting sequence was compared to sequences in the GenEMBL database using the FASTA and TFASTA search routines of the GCG sequence analysis package from the University of Wisconsin. There was sequence similarity between the isolated DNA and the DnaJ or DnaJ related protein genes from bacteria, yeast, mammals and three recently published plant sequences.

The F3.7 cDNA was then used as a probe to obtain the corresponding genomic clone as follows. A 230 bp EcoRI/ScaI fragment and a 480 bp XhoI/XbaI fragment which corresponded to the 5' and 3' ends respectively were isolated and labeled with digoxigenin-11-dUTP by the random primer method according to the Genius™ system users guide (Boehringer Mannheim, Indianapolis, Ind.). Two positive clones were recovered from approximately $1\times10^6$ plaques from a maize genomic library constructed in lambda DASH (Stratagene, La Jolla, Calif.).

One of the two hybridizing clones was studied to obtain a partial restriction map; three fragments from a SacI/Xhol digest were subcloned into pGEM7Zf(+) (Promega, Madison, Wis.) and were completely sequenced.

The sequence information in combination with sequence alignment to other published DnaJ or DnaJ related cDNA clones was used to determine the putative translation initiation codon. Based on this information, oligonucleotide primers were constructed to amplify 812 base pairs of the 5' region directly upstream from the putative translation initiation codon. Oligonucleotide D02444 (5'-GGGTTTGAGCTCAAGCCGCAACAACAAAT) (SEQ ID NO: 4 corresponds to the 5' end of the putative promoter and includes the native maize SacI site. Oligonucleotide D02445 (5'-GGGTTAGATCTAGACTTGCCTTTGCCTCCGG CGGT) (SEQ ID NO: 5) corresponds to the antisense strand at the 3' end of the putative promoter and contains introduced sequences for XbaI and BglII restriction sites. Using these primers, the promoter portion of the genomic clone was amplified.

The DNA sequence of 3748 nucleotides for the recovered genomic clone is shown in FIG. 2. The 812 nucleotide 5' untranslated region containing the promoter is shown in FIG. 1.

It will be noted that the promoter region contains no obvious TATAA or CCAAT-like sequences and is also very

EXAMPLE 2

Use in Expression

A sample of the PCR amplified promoter was digested with SacI and XbaI and cloned into the corresponding sites in the multiple cloning sequence of pBlueScript SK+ (Stratagene, La Jolla, Calif.) to produce vector pPHI5896. A second sample of the promoter was digested with SacI and BglII combined with a 2188 bp BamHI/EcoRI fragment containing the uidA (GUS) gene fused to the 3' terminating region from potato proteinase inhibitor (PinII), and these fragments were cloned together into SacI/EcoRI digested pBlueScript SK+ to obtain pPHI5897, diagramed in FIG. 3. A third sample of the promoter was digested with SacI/BglII and combined with (1) a BglII/StuI fragment containing the synthetic equivalent of the BT cryIIA gene preceded by a synthetic equivalent of a 15 kD maize zein targeting sequence; (2) a HpaI/EcoRI fragment containing the PinII 3' terminator, and (3) pBlueScript SK+ cut with SacI/EcoRI. The combination of these four elements generated pPHI5898, diagramed in FIG. 4. Thus, pPHI5897 contains an expression system for the GUS marker and pPHI5898 contains an expression system for BT cryIIA.

Suspension cultures of the maize Black Mexican Sweet (BMS) variety, as well as regenerable maize HiII callus cultures, were transformed with pPHI5897 or an insert region from pPHI5898 lacking the BlueScript vector sequences. A selectable marker gene-containing vector was cobombarded to provide selection of transformed cells. This vector contains the PAT selectable marker behind the CaMV35S promoter. In parallel experiments, vectors or inserts containing the uida or cryIIA gene under control of the CaMV 35S promoter were transformed into the plant cells.

After bombardment, BMS callus events were transferred to nonselective media and incubated in the dark for two days then resuspended and plated onto selection media containing 25 mg/L BASTA (Hoescht, Germany).

Postbombardment Hi-II culture events were incubated at 27° C. in the dark for six days followed by transfer to selection media containing 3 mg/L bialophos (Meiji Seika, Japan). About six weeks later putative transformed colonies were transferred onto regeneration media and after several weeks developing embryos or scutellar structures were transferred and cultured separately in the light. Transgenic maize plantlets were thus recovered.

Both the expression systems containing the control sequence of the invention, and the control expression systems containing CaMV 35S showed strong GUS expression in callus cultures 24 hours after addition of the substrate solution wherein the transgenic callus or Hi-II plant tissues were sampled and incubated for 24 hours in McCabe's stain. GUS expression was detectable as early as four hours. The level of expression for the promoter of the invention appeared to be about 50% of that effected by the CaMV 35S promoter. Additionally, tissues from plants grown to maturity (4–8 days postpollination) were scored for GUS expression both histochemically and by semiquantitative determination of GUS protein in tissues. Significant amounts of GUS were detected in most tissues examined including flag leaf, midplant leaf, upper and lower stem, root, kernel and cob, with some events also expressing in anther tissues or in pollen. This expression was observed in several independent transformation events, with some relative variation between events.

In a similar manner, plantlets transformed with pPHI5898 as BMS callus positive events or plants from Hi-II positive events are used in feeding bioassays. Larvae are allowed to feed ad libitum on the transgenic tissues or equivalent non-cryIIA containing tissues. Insect weight loss and mortality are scored and show that the BT protein is produced under control of the invention promoter. Expression of BT protein in transgenic plant tissues was confirmed by Western analysis of protein extracts. The amount of BT protein was also assessed using ELISA assays.

---

We claim:

1. A purified and isolated DNA molecule comprising the transcriptional promoter and/or the leader sequence of the nucleotide sequence of the control sequence shown in positions −812 to −1 of SEQ ID NO: 1.

2. The DNA molecule of claim 1 which comprises the nucleotide sequence of the control sequence shown in positions −812 to −1 of SEQ ID NO: 1.

3. A composition of DNA molecules consisting of DNA molecules which contain the transcriptional promoter and/or the leader sequence of the nucleotide sequence shown as positions −812 to −1 in SEQ ID NO: 1.

4. The composition of claim 3 wherein said DNA molecules contain the nucleotide sequence shown as positions −812 to −1 in SEQ ID NO: 1.

5. A recombinant expression system which comprises the transcriptional promoter and/or the leader sequence of the nucleotide sequence shown as positions −812 to −1 in SEQ ID NO: 1 operably linked to the coding sequence for a desired protein heterologous to said nucleotide sequence.

6. The expression system of claim 5 which comprises the nucleotide sequence shown as positions −812 to −1 in SEQ ID NO: 1 operably linked to the coding sequence for a desired protein heterologous to said nucleotide sequence.

7. The expression system of claim 5 wherein said desired protein is an insecticidal protein or an antifungal protein.

8. The expression system of claim 6 wherein said desired protein is an antifungal protein or an insecticidal protein.

9. A plant, plant part, or plant cell, wherein said plant is a monocot modified to contain the expression system of claim 5.

10. A plant, plant part, or plant cell, wherein said plant is a monocot modified to contain the expression system of claim 6.

11. A method to protect monocot plants against insects or fungi which method comprises modifying said plants to contain the expression system of claim 7 and culturing the plants under conditions for expression of said coding sequence.

12. A method to protect monocot plants against insects or fungi which method comprises modifying said plants to contain the expression system of claim 8 and culturing the plants under conditions for expression of said coding sequence.

13. A purified and isolated DNA comprising fragments of the control sequence shown in positions −812 to −1 of SEQ ID NO: 1 which retain transcription-initiating activity and/or the function of the leader sequence.

14. A method to regulate the expression of a gene under control of the ZMDJ1 control sequence in plant cell, plant parts or plants, wherein said plant is a monocot, which method comprises modifying said cell, part or plant containing said gene under control of said ZMDJ1 control sequence to contain the DNA of claim 13 or RNA of the same nucleotide sequence.

15. The method of claim 14 wherein said RNA is provided by modifying said cell, part or plant to contain an expression system for said RNA.

16. A plant cell, plant part or plant, wherein said plant is a monocot, modified to contain the DNA or RNA of claim 14.

\* \* \* \* \*

UNITED STATES PATENT AND TRADEMARK OFFICE
CERTIFICATE OF CORRECTION

PATENT : 5,850,018
DATED : December 15, 1998
INVENTOR(S): Chris Baszczynski, Eric Barbour, Jeannine Horowitz, and Jeffrey L. Rosichan

It is certified that error appears in the above-identified patent and that said Letters Patent is hereby corrected as shown below:

On the title page, item [60] delete the following:

"Provisional application No. 60/001,552 Jul. 27, 1995.", and
insert therefor --Provisional application No. 60/001,522, Jul. 26, 1995.--; and In column 1, lines 5 and 6, delete "This application claims the benefit of U.S. Provisional Application No. 60/001,552, filed Jul. 27, 1995.", and insert therefor --This application claims the benefit of U.S. Provisional Application No. 60/001,522, filed Jul. 26, 1995.

Signed and Sealed this

Fifteenth Day of June, 1999

Attest:

Q. TODD DICKINSON

*Attesting Officer*   Acting Commissioner of Patents and Trademarks

UNITED STATES PATENT AND TRADEMARK OFFICE
CERTIFICATE OF CORRECTION

PATENT NO : 5,850,018
DATED : Dec. 15, 1998
INVENTOR(S): Chris Baszczynski, Eric Barbour, Jeannine Horowitz, Jeffrey Rosichan It is certified that error appears in the above-identified patent and that said Letters Patent is hereby corrected as shown below:

FIG. 3 (word below 2000)
    GUS

Figure 4:
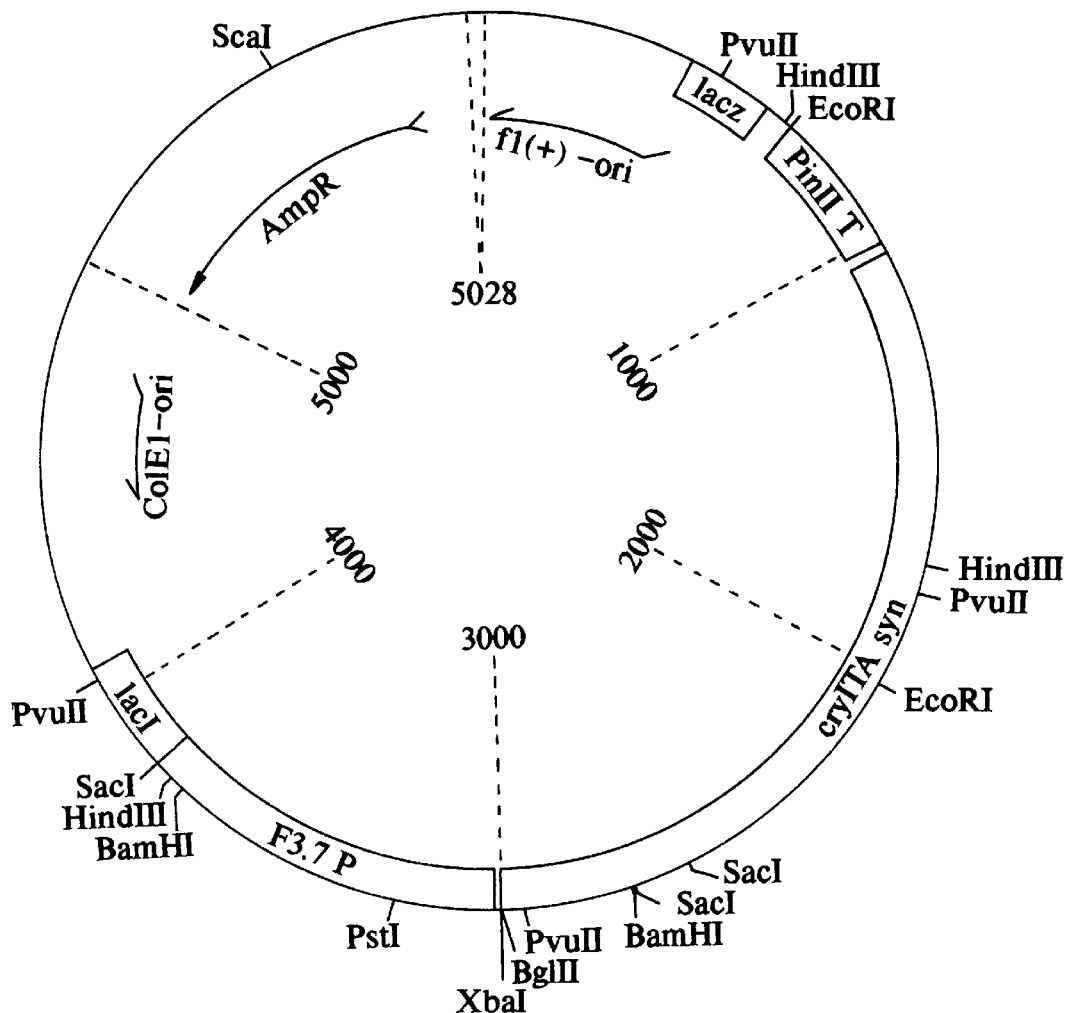
FIG. 4 is a diagram of pPH15898.

FIG. 4 (word below 2000)
    CryIIA syn

Signed and Sealed this

Fourth Day of July, 2000

Attest:

Q. TODD DICKINSON

Attesting Officer      Director of Patents and Trademarks